United States Patent
Matsuoka et al.

(10) Patent No.: US 12,253,494 B2
(45) Date of Patent: Mar. 18, 2025

(54) INFORMATION PROCESSING APPARATUS, INFORMATION PROCESSING METHOD, LEARNED MODEL GENERATION METHOD, AND PROGRAM

(71) Applicant: REVORN CO., LTD., Tokyo (JP)

(72) Inventors: Hiroaki Matsuoka, Tokyo (JP); Noriaki Koide, Tokyo (JP); Yusuke Kosuda, Tokyo (JP)

(73) Assignee: REVORN CO., LTD. (JP)

( * ) Notice: Subject to any disclaimer, the term of this patent is extended or adjusted under 35 U.S.C. 154(b) by 540 days.

(21) Appl. No.: 17/297,842

(22) PCT Filed: Dec. 4, 2019

(86) PCT No.: PCT/JP2019/047343
§ 371 (c)(1),
(2) Date: May 27, 2021

(87) PCT Pub. No.: WO2020/116490
PCT Pub. Date: Jun. 11, 2020

(65) Prior Publication Data
US 2021/0325343 A1   Oct. 21, 2021

(51) Int. Cl.
*G01N 29/02* (2006.01)
*G01N 29/44* (2006.01)
*G06N 20/00* (2019.01)

(52) U.S. Cl.
CPC ....... *G01N 29/022* (2013.01); *G01N 29/4454* (2013.01); *G01N 29/4472* (2013.01); *G06N 20/00* (2019.01); *G01N 2291/021* (2013.01)

(58) Field of Classification Search
CPC ............ G01N 29/022; G01N 29/4454; G01N 29/4472; G01N 2291/021; G01N 33/0034;
(Continued)

(56) References Cited

U.S. PATENT DOCUMENTS

| | | | | |
|---|---|---|---|---|
| 11,644,449 B2 * | 5/2023 | Onda | ................. | G01N 33/0001 73/23.34 |
| 2004/0135684 A1 * | 7/2004 | Steinthal | ............ | G01N 33/0034 340/522 |

(Continued)

FOREIGN PATENT DOCUMENTS

| | | |
|---|---|---|
| CN | 103868955 A | 6/2014 |
| JP | H05-010904 A | 1/1993 |

(Continued)

OTHER PUBLICATIONS

Matsuno et al. (A Quartz Crystal Microbalance-Type Odor Sensor Using PVC-Blended Lipid Membrane, IEEE, 1995) (Year: 1995).*
(Continued)

*Primary Examiner* — Mohammad K Islam
(74) *Attorney, Agent, or Firm* — Harness, Dickey & Pierce, P.L.C.

(57) ABSTRACT

An information processing apparatus includes: a first acquisition unit that acquires odor data obtained by measuring the odor of an object; a second acquisition unit that acquires an acquisition condition for the odor data; and an identification unit that identifies the object from the odor data and the acquisition condition acquired by the first and second acquisition units on the basis of a learned model obtained by performing learning on the odor data of the object and the acquisition condition, and on the object corresponding to the odor data. The acquisition condition can be text data that indicates the category of the odor and is inputted by a user who has measured the odor.

13 Claims, 12 Drawing Sheets

(58) Field of Classification Search
CPC .... G01N 33/0004; G06N 20/00; G06N 3/044; G06N 3/084
See application file for complete search history.

(56) References Cited

U.S. PATENT DOCUMENTS

| | | | |
|---|---|---|---|
| 2006/0191319 A1* | 8/2006 | Kurup | G01N 33/0034 73/23.34 |
| 2013/0154797 A1* | 6/2013 | Lee | G05B 1/00 340/5.74 |
| 2018/0137462 A1* | 5/2018 | Zohar | G06Q 10/0875 |
| 2019/0019033 A1* | 1/2019 | Chang | G06V 10/809 |
| 2019/0087425 A1* | 3/2019 | Kim | G06N 3/08 |
| 2020/0097776 A1* | 3/2020 | Kim | G06T 7/70 |
| 2020/0300798 A1* | 9/2020 | Watanabe | G01N 27/122 |

FOREIGN PATENT DOCUMENTS

| | | |
|---|---|---|
| JP | H6-160317 A | 6/1994 |
| JP | 2007-022169 A | 2/2007 |
| JP | 2011-169830 A | 9/2011 |
| JP | 2017-161300 A | 9/2017 |
| JP | 2018-045517 A | 3/2018 |
| JP | 2018-075255 A | 5/2018 |
| JP | 2018-146803 A | 9/2018 |
| WO | 2016-060863 A2 | 4/2016 |
| WO | 2016-060863 A3 | 4/2016 |
| WO | WO-2016145300 A1 * | 9/2016 |

OTHER PUBLICATIONS

Nanto (Odor sensor using quartz crystal microbalance coated with molecular recognition membrane, 2006) (Year: 2006).*

Acharyya D. et al. "Noise Analysis-Resonant Frequency-Based Combined Approach for Concomitant Detection of Unknown Vapor Type and Concentration"; IEEE Transactions on Instrumentation and Measurement, IEEE, USA; vol. 68, No. 8; published on Sep. 18, 2018; pp. 3004-3011 (total 8 pages).

Extended European Search Report issued for the corresponding European Application No. 19891914.4; dated Jan. 17, 2022 (total 11 pages).

International Search Report (English and Japanese) of the International Searching Authority issued in PCT/JP2019/047343, mailed Mar. 3, 2020; ISA/JP (6 pages).

Office Action issued in the corresponding Chinese Patent Application No. 201980080060.X; dated Nov. 29, 2023 (total 42 pages).

"New technology to raise manhood. Kunkun body realizes odor management fo capable men"; Konica Minolta BIC—Japan; URL: https://www.makuake.com/project/kunkunbody/; Author unknown; retrived from the internet on Feb. 29, 2024 (total 42 pages).

English abstract; Young Ah Seong, et al. "Scent Sensing System for Recording Scent Data in Daily Life"; Transactions of the Virtual Reality Society of Japan; vol. 16, No. 4; dated Dec. 31, 2011; pp. 677-686 (total 10 pages).

"Scent AI startup Revorn launches "iinioi Project" utilizing the world's No. 1 scent database and AI"; PR Times; URL: https://prtimes.jp/main/html/rd/p/00; published online by PR Times Corporation on Nov. 20, 2018; retrieved online on Feb. 9, 2024 (total 14 pages).

Office Action issued in the corresponding Japanese Patent Application No. 2020-559951; mailed on Mar. 5, 2024 (total 8 pages).

Amy Loutfi et al. "Object recognition: A new application for smelling robots"; Robotics and Autonomous Systems; vol. 52, No. 4; Sep. 30, 2005; pp. 272-289; XP027792856; ISSN: 0921-8890 (total 18 pages).

Amy Loutfi et al. "Putting Olfaction into Action: Anchoring Symbols to Sensor Data Using Olfaction and Planning"; ReasearchGate; Oct. 23, 2004; pp. 1-7; XP093134143 (total 7 pages).

Amy Loutfi et al. "Odor source identification by grounding linguistic descriptions in an artificial nose"; Proceedings of SPIE; vol. 4385; Mar. 22, 2001; pp. 273-281; XP093134136; ISSN: 0277-786X; DOI: 10.1117/12.421115 (total 10 pages).

Office Action issued in the corresponding European Patent Application No. 19891914.4; dated Feb. 28, 2024 (total 9 pages).

Liu Yande, "Non-destructive Intelligent Inspection Technology and Application"; Huazhong University of Science and Technology Publishing House; May 1, 2007; pp. 245-247 (total 18 pages).

Office Action issued in the corresponding Chinese Patent Application No. 201980080060.X; dated Nov. 29, 2024 (total 26 pages).

* cited by examiner

FIG. 9

| | | | | | | | | | |
|---|---|---|---|---|---|---|---|---|---|
| | | | | | | | LIST OF DATA | ACQUIRE DATA | LEARNED DATA | UPLOAD |

MEASURE

LIST OF DATA

DETERMINATION

DATA VISUALIZATION

AI LEARNING

SETTING

ACQUIRE DATA

KEYWORD

DOMAIN

SUBDOMAIN

ACQUIRED DATE AND TIME

YYYY/MM/DD ~ YYYY/MM/DD

SEARCH  DOWNLOAD

| ODOR NAME | DOMAIN NAME | SUB DOMAIN NAME | ACQUIRED DATE AND TIME | NUMBER OF DATA | PRE-CLEANING (SECOND) | SUCTION (SECOND) | RESIDENCE (SECOND) | POST-CLEANING (SECOND) | ACQUIRED USER | ACQUIRED SENSOR | SELECT |
|---|---|---|---|---|---|---|---|---|---|---|---|
| xxx | xxx | xxx | 2019/10/8 11:04:53 | 0 | 300 | 120 | 120 | 300 | xxx | xxx | ○ |
| xxx | xxx | xxx | 2019/10/8 11:04:53 | 0 | 300 | 120 | 120 | 300 | xxx | xxx | ○ |
| xxx | xxx | xxx | 2019/10/8 11:04:53 | 0 | 300 | 120 | 120 | 300 | xxx | xxx | ○ |
| xxx | xxx | xxx | 2019/10/8 11:04:53 | 0 | 300 | 120 | 120 | 300 | xxx | xxx | ○ |
| xxx | xxx | xxx | 2019/10/8 11:04:52 | 0 | 300 | 120 | 120 | 300 | xxx | xxx | ○ |
| xxx | xxx | xxx | 2019/10/8 | 0 | 300 | 120 | 120 | 300 | xxx | xxx | ○ |

INFORMATION PROCESSING APPARATUS, INFORMATION PROCESSING METHOD, LEARNED MODEL GENERATION METHOD, AND PROGRAM

CROSS REFERENCE TO RELATED APPLICATIONS

This is a U.S. National Phase Application under 35 U.S.C. 371 of International Application No. PCT/JP2019/047343, filed on Dec. 4, 2019, which claims priority to U.S. Patent Application No. 62/775,561, filed on Dec. 5, 2018. The entire disclosures of the above applications are expressly incorporated by reference herein.

BACKGROUND

Technical Field

The present invention relates to an information processing apparatus, an information processing method, a learned model generation method, and a program.

Related Art

There is a technology for performing object identification based on odor of the object. For example, JP 2017-161300 discloses an odor identification system for identifying a passenger seated on a seat of a vehicle using a neural network based on a signal detected by an odor detection apparatus installed in a sheet.

However, the invention according to JP 2017-161300 has not identified in consideration of the conditions when the odor is measured.

SUMMARY

In one aspect, the present invention aims to provide an information processing apparatus or the like capable of preferably identifying an object from the odor of an object.

An information processing apparatus according to one aspect comprises a first acquisition unit configured to acquire odor data measuring an odor of an object, a second acquisition unit configured to acquire an acquisition condition of the odor data, and an identification unit configured to identify the object from the odor data and the acquisition condition acquired by the first and second acquisition units based on the learned model that has learned the odor data and the acquisition condition of the object and the object corresponding to the odor data.

In one aspect, an object can be suitably identified from the odor of the object.

BRIEF DESCRIPTION OF THE DRAWINGS

FIG. 9 is an explanatory diagram showing an example of a list screen of odor data.

DETAILED DESCRIPTION

Hereinafter, embodiments of the present invention will be described with reference to the drawings.

FIRST EMBODIMENT

Figure 1:
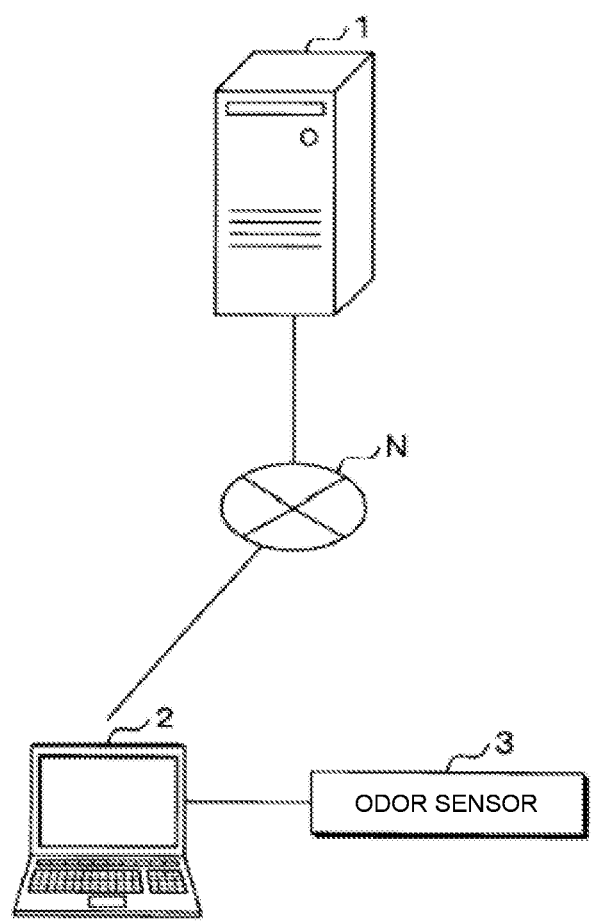
FIG. 1 is a schematic diagram showing a configuration example of an odor identification system.

FIG. 1 is a schematic diagram showing a configuration example of an odor identification system. In the present embodiment, an odor identification system that identifies objects from odor data using an identification model 141 (learned model, see FIG. 5) that has been learned by machine learning on odor data that measures odor of objects will be described. The odor identification system includes an information processing apparatus (analysis management apparatus) 1, a terminal 2, and an odor sensor 3. The information processing apparatus 1 and the terminal 2 are connected to a network N such as internet.

The information processing apparatus 1 is an information processing apparatus that can perform various information processing and send/receive information, such as server computer or personal computer. In the present embodiment, it is assumed that the information processing apparatus 1 is a server computer, and it will be read as server 1 in the following description for the sake of brevity. The server 1 is a server computer that analyzes and manages odor data of objects arbitrarily uploaded by users, and performs machine learning to learn the odor data and generates an identification model 141 to identify objects from the odor data. Then, the server 1 identifies the object using the generated identification model 141. For instance, if the object is human, the server 1 identifies the person based on the measured odor data of exhalation odor of the person. Note that person identification is only one example of the use of the system, and the system may be used to identify other objects.

The terminal 2 is a terminal apparatus used by users of this system, such as personal computer, tablet, or smartphone. The server 1 obtains odor data of objects from the odor sensor 3 via the terminal 2, performs identification by the identification model 141, and outputs the identification results to the terminal 2.

The odor sensor 3 is a sensor that measures the odor of an object, and converts gas molecules corresponding to odor components into numerical values that can be processed by a computer. For example, the odor sensor 3 is an odor sensor using the QCM (Quartz Crystal Microbalance) method, which converts odor components into frequency data by using the oscillation of a quartz crystal when gas molecules are adsorbed on the surface of the quartz crystal. The use of an odor sensor using the quartz crystal as the odor sensor 3 makes it possible to obtain odor data that is closer to the human sense of odor than that of semiconductor-type odor sensors that measure the resistance of semiconductors or biosensors that use FETs (field effect transistors). The odor sensor 3 is connected to the terminal 2 of the user, and the server 1 obtains the odor data measured by the odor sensor 3.

The odor sensor 3 itself may be equipped with a communication module so that the server 1 can obtain odor data directly from the odor sensor 3. The odor sensor 3 is not limited to the odor sensor with the quartz crystal, but may also be semiconductor type odor sensor, FET biosensor, or the like.

Figure 2:
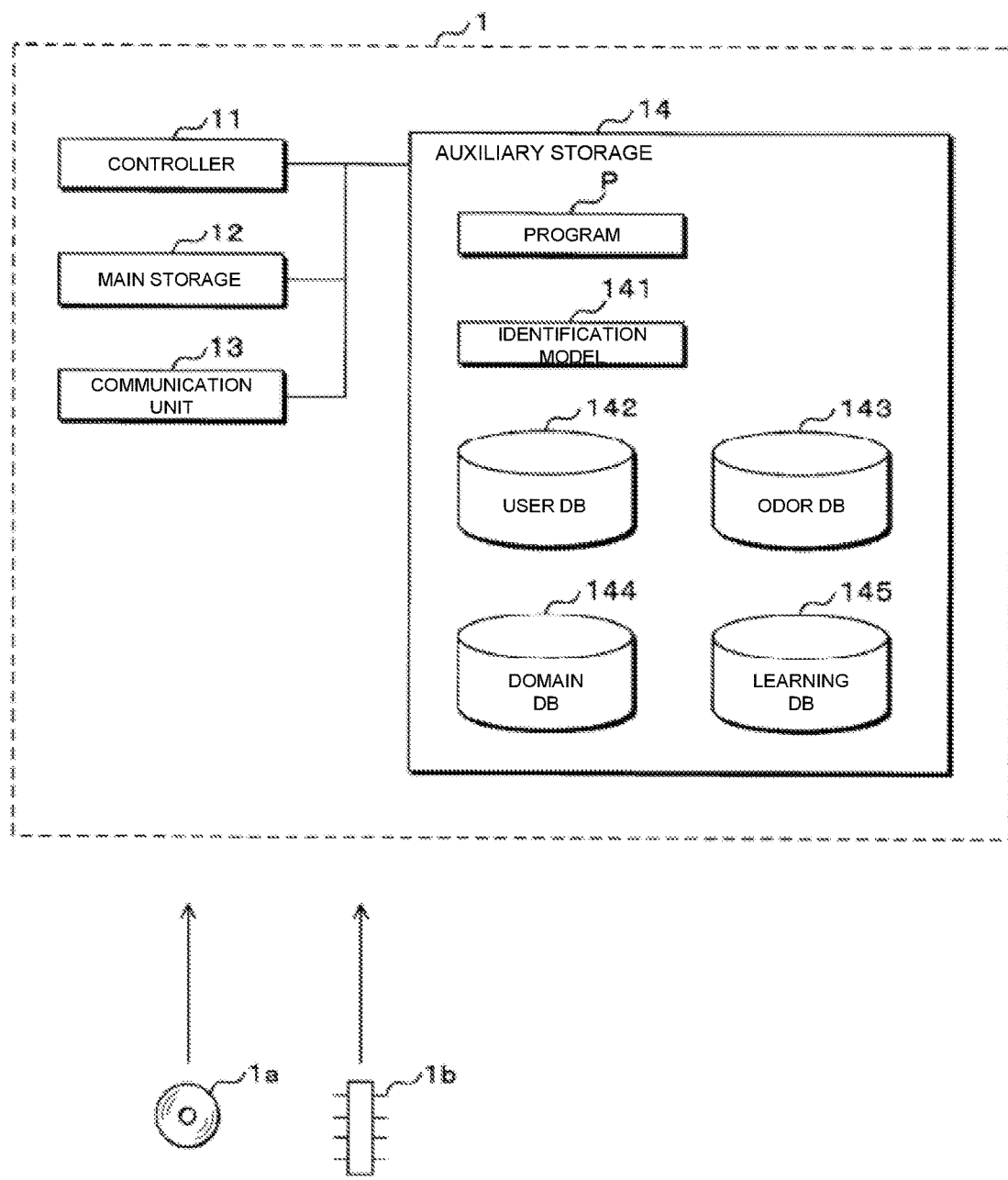
FIG. 2 is a block diagram showing a configuration example of a server.

FIG. 2 is a block diagram showing a configuration example of the server 1. The server 1 has a controller 11, a main storage 12, a communication unit 13, and an auxiliary storage 14. The controller 11 has one or more arithmetic processing units such as CPU (Central Processing Unit), MPU (Micro-Processing Unit), or GPU (Graphics Processing Unit), and performs various information processing or control processing or the like by reading and executing program P stored in the auxiliary storage 14. The main memory 12 unit is a temporary storage area such as SRAM (Static Random Access Memory), DRAM (Dynamic Random Access Memory), or flash memory, and temporarily stores data necessary for the controller 11 to perform arithmetic processing. The communication unit 13 is a communication module for executing processing related to communication and sends/receives information to and from the outside.

The auxiliary storage 14 is a non-volatile storage area such as large-capacity memory or hard disk, and stores the program P and other data necessary for the controller 11 to execute processing. Further, the auxiliary storage 14 stores the identification model 141, user DB 142, odor DB 143, domain DB 144, and learning DB 145. The identification model 141 is a model for object identification based on the odor data. The identification model 141 is, for example, a model related to neural network to be described later. The identification model 141 is assumed to be used as a program module that is part of artificial intelligence software. The user DB 142 is a database that stores information of each user who uses this system. Odor DB 143 is a database that stores odor data acquired from the odor sensors 3. The domain DB 144 is a database that stores information of domains (odor categories) to be described later. The learning DB 145 is a database that stores learned parameters obtained by learning odor data, such as weights that are set in the identification model 141 (neural network).

The auxiliary storage 14 may be an external storage connected to the server 1. The server 1 may be a multi-computer comprises multiple computers, or may be a virtual machine virtually built by software.

Further, in the present embodiment, the server 1 is not limited to the above configuration, but may include, for example, an input unit to receive operation input, a display unit to display images, etc. In addition, the server 1 may has a reading unit that reads and executes a portable storage medium 1a such as CD (Compact Disk)-ROM or DVD (Digital Versatile Disc)-ROM, and reads and executes the program P from the portable storage medium 1a. Alternatively, the server 1 may read the program P from a semiconductor memory 1b.

Figure 3:
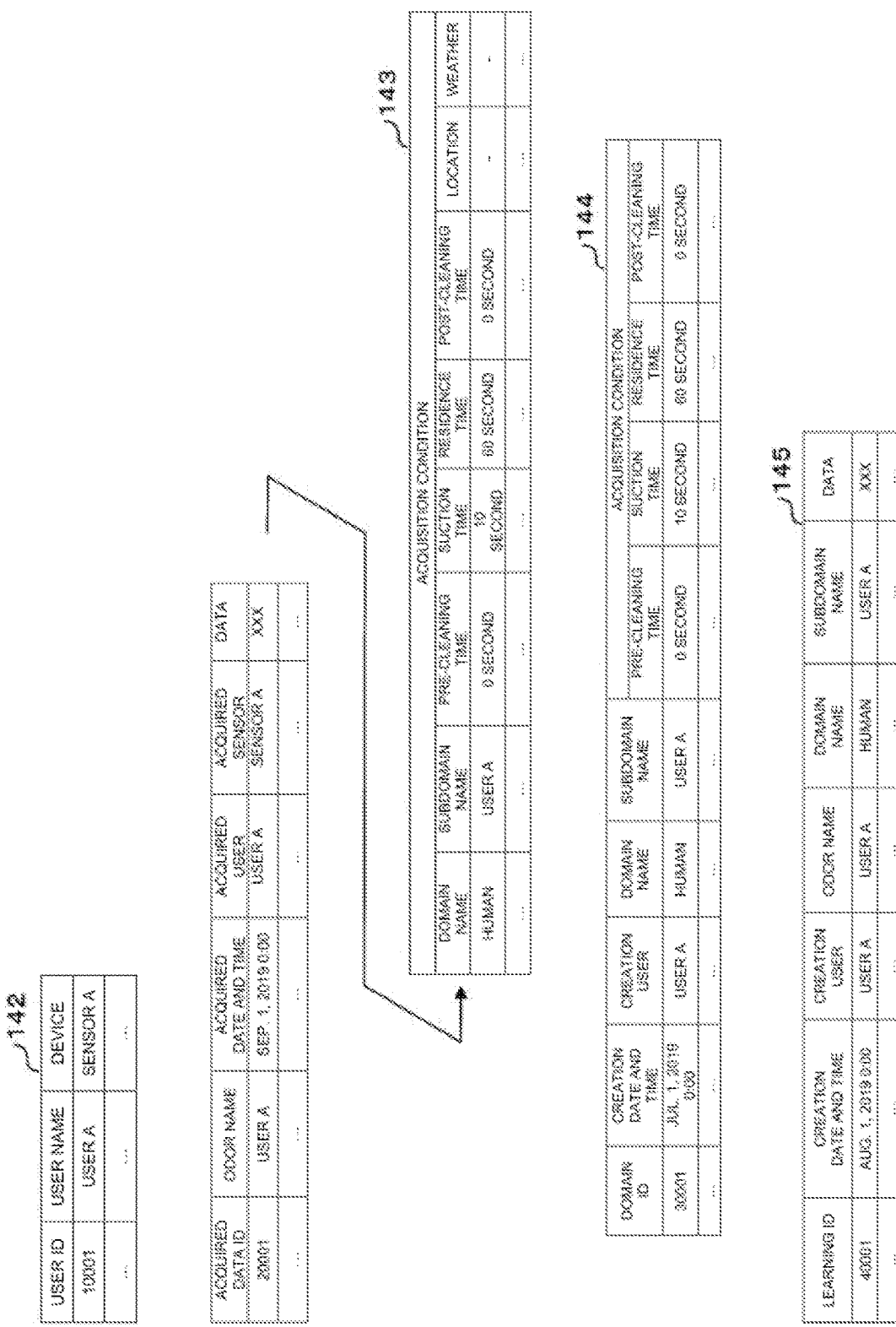
FIG. 3 is an explanatory diagram showing an example of a record layout of a user DB, an odor DB, a domain DB, and a learning DB.

FIG. 3 is an explanatory diagram showing an example of a record layout of the user DB 142, the odor DB 143, the domain DB 144, and the learning DB 145. The user DB 142 includes a user ID column, a user name column, and a device column. The user ID column stores the user ID, which is an identifier of each user. The user name column and the device column store the user name and the name of the odor sensor 3 used by the user, respectively, in correspondence with the user ID.

The odor DB 143 includes an acquisition data ID column, an odor name column, an acquisition date and time column, an acquisition user column, an acquisition sensor column, a data column, and an acquisition condition column. The acquisition data ID column stores the acquisition data ID, which is an identifier of the odor data acquired from the odor sensor 3. The odor name column, the acquisition date and time column, the acquisition user column, the acquisition sensor column, the data column, and the acquisition condition column store the odor name (object name), the acquisition date and time, the user name from which the odor data was acquired, the name of the odor sensor 3 from which the odor data was acquired, the odor data, and the acquisition condition of the odor data, respectively, in correspondence with the acquisition data ID. The acquisition condition column stores, for example, the domain name and subdomain name to be described later, the cleaning time when the odor sensor 3 was cleaned before measurement, the suction time of the odor (gas), the residence time in the gas chamber in the odor sensor 3, the cleaning time of the odor sensor 3 after measurement, the location information of the place where the odor was measured, and the weather information of the place. Various information that defines the acquisition conditions of the odor data will be described in detail later.

The domain DB 144 includes a domain ID column, a creation date and time column, a creation user column, a domain name column, a subdomain name column, and an acquisition condition column. The domain ID column stores the domain ID, which is an identifier of a domain indicating category of odor. The creation date and time column, the creation user column, the domain name column, the subdomain name column, and the acquisition condition column store the date and time when the user registering (creating) the information of the domain in the system, the registered user name, the domain name, the subdomain name, and the measurement conditions (acquisition conditions) in the odor sensor 3, respectively, in correspondence with the domain ID. The acquisition conditions store, for example, pre-cleaning time before odor measurement, suction time, residence time, and post-cleaning time after odor measurement.

The learning DB 145 includes a learning ID column, a creation date and time column, a creation user column, a odor name column, a domain name column, a subdomain name column, and a data column. The learning ID column stores the learning ID, which is an identifier of the learned parameter (such as the weight of the neural network) obtained by learning the odor data. The creation date and time column, the creation user column, the odor name column, the domain name column, the subdomain name column, and the data column store the creation date and time when the learning (creation) of the identification model 141 was executed, user name of the user who performed the learning of the identification model 141, the odor name that was learned, the domain name and subdomain name indicating the acquisition conditions of learned odor data, and learned parameters, respectively, in correspondence with the learning ID.

Figure 4:
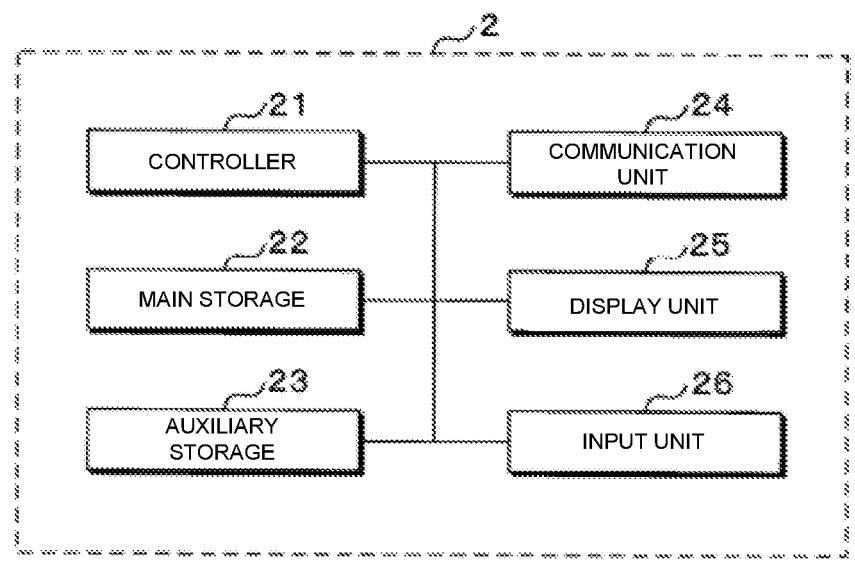
FIG. 4 is a block diagram showing a configuration example of a terminal.

FIG. 4 is a block diagram showing a configuration example of the terminal 2. The terminal 2 includes a controller 21, a main storage 22, an auxiliary storage 23, a communication unit 24, a display unit 25, and an input unit 26.

The controller 21 has an arithmetic processing unit such as CPU and executes various information processing and control processing by reading and executing program stored in the auxiliary storage 23. The main storage 22 is a temporary storage area such as RAM and temporarily stores data necessary for the controller 21 to execute arithmetic processing. The auxiliary storage 23 is a non-volatile storage area such as ROM (Read-Only Memory) and stores program and other data necessary for the controller 21 to execute processing. The communication unit 24 is a communication module for executing processing related to communication and sends/receives information to/from the outside. The display unit 25 is a display screen such as liquid crystal display and displays images given by the controller 21. The input unit 26 is an operation interface such as mechanical key and receives operation input from the user.

Figure 5:
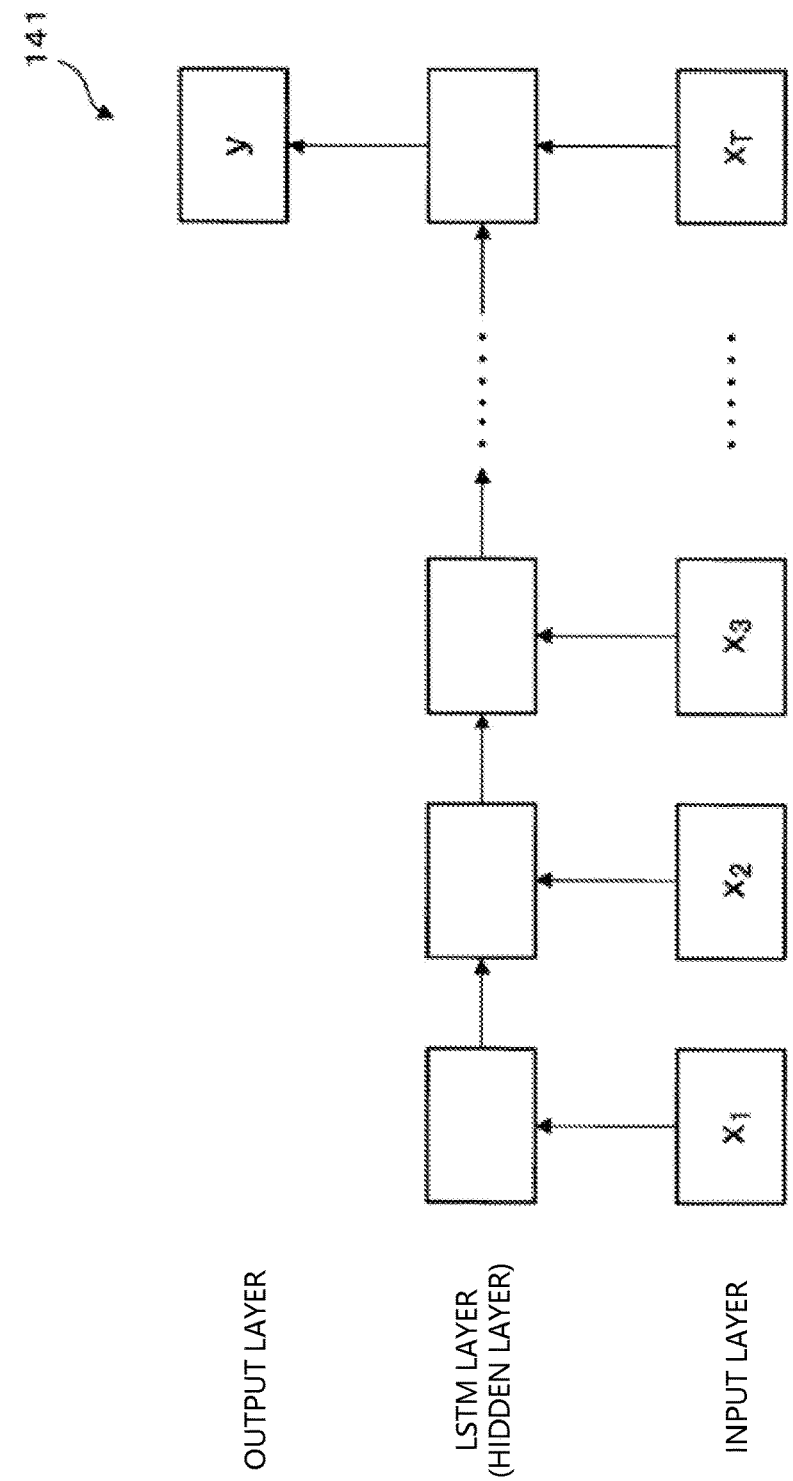
FIG. 5 is an explanatory diagram of an identification model.

FIG. 5 is an explanatory diagram of the identification model 141. An overview of the embodiment will be described based on FIG. 5. In the present embodiment, the server 1 uses a neural network model generated by deep learning as the identification model 141. Specifically, the identification model 141 is a model related to LSTM (Long-Short Term Memory), which is a type of RNN (Recurrent Neural Network), and is a model that inputs time-series data comprising data at multiple time points.

The identification model 141 has an input layer that accepts input of time-series data, an intermediate layer (hidden layer) that extracts features from the data input to the input layer, and an output layer that outputs identification results based on the features. The input layer has neurons that accept input of data at each of multiple consecutive time points, and the neurons in the input layer pass the input data to the neurons in the intermediate layer. The intermediate layer receives input data from the neurons in the input layer and executes operation based on the input data. In LSTM, the neurons in the intermediate layer are called LSTM blocks, and they temporarily store the results of their own operations. When executing an operation regarding the input data at the next time point, the operation is executed by referring to the operation result of the input data at the previous time point. By referring to the operation result at the previous time point, the operation of the next time point is executed from the time-series data up to the most recent time point. The output layer has neurons that operate the output value based on the operation result in the intermediate layer, and outputs the identification result of the object.

In the present embodiment, the identification model 141 is assumed to be a model with one output in correspondence with multiple inputs (Many-To-One), but it may have multiple outputs. Further, the identification model 141 propagates the operation result of the intermediate layer only in one direction (One-directional) from the past time point to the future time point, but it may be a model that propagates operation result in both directions (Bi-directional).

Although the identification model 141 is described as LSTM in the present embodiment, it may be a model based on other learning algorithms, for example, other deep learning such as CNN (Convolution Neural Network), SVM (Support Vector Machine), decision tree, or the like.

In the present embodiment, the server 1 generates the identification model 141 that inputs the odor data measured the odor of the object and outputs the identification result of the object corresponding to the input odor data. The odor data input to the identification model 141 is the data measured by the odor sensor 3 described above, and is a time series data of frequency measured by QCM method. For example, the odor sensor 3 measures the gas (odor) inhaled into the gas chamber in the odor sensor 3 between measurement time of several seconds to several tens of seconds and obtains the time series data of the frequency over the measurement time. The server 1 uses the data as odor data.

For example, the server 1 receives an upload of odor data measured by the odor sensor 3 from the terminal 2 of each user, and stores the odor data in the odor DB 143 in correspondence with the odor name indicating the object for which the odor was measured and the acquisition condition of the odor data to be described later. The server 1 uses the odor data stored in the odor DB 143 as training data to generate the identification model 141.

That is, the server 1 sequentially inputs the time series odor data measured by the odor sensor 3 to each neuron in the input layer of the identification model 141 according to the time series order at the time of the measurement, and obtains the output value indicating the identification result of the object from the output layer after the operation in the intermediate layer. In the present embodiment, the server 1 considers the object corresponding to the odor data input to the input layer as a two-class classification problem to determine whether or not the object corresponds to a specific object to be learned, and outputs a probability value indicating whether or not it corresponds to the object. By performing the identification of a single object per a single identification model 141, the identification accuracy can be improved compared to the case of multi-class classification in which a single identification model 141 is used to identify multiple objects.

The output value from the identification model 141 may not be a probability value but a value that indicates whether or not it corresponds to the object by a binary value (0 or 1). Further, in the present embodiment, two-class classification is used to determine whether or not the object corresponds to one object, but the model may be used for multi-class classification by simultaneously learning the odor data of multiple objects as training data.

Here, the server 1 performs learning by using not only the odor data measured by the odor sensor 3 but also the acquisition condition of the odor data input to the identification model 141. The acquisition condition of the odor data is information that indicates the condition under which the odor data was measured, and includes, for example, text data that indicates the category of the measured odor, state information that indicates the state of the odor sensor 3 from which the odor data was acquired, and environmental information related to measurement environment when the odor was measured.

The odor category is information that indicates, for example, type of object for which the odor was measured, or the state of the object at the time of odor measurement (for example, if the object is food, the number of days since the food was purchased). These are just examples, and the odor category may be defined arbitrarily. In the present embodiment, the odor category is set by the user who has measured the odor of an object by entering an arbitrary text. In the system, the odor category arbitrarily set by the user is called as "domain".

For example, the server 1 obtains the domain name arbitrarily input by the user as indicating the odor category when receiving an upload of the odor data from the terminal 2. Specifically, the server 1 acquires the domain name that indicates the odor category and the subdomain name that indicates a further detailed category than the domain name. As an example, the type name of the object for which the odor was measured ("human" in the example of person identification) is input as the domain name, and a more detailed type name than the domain name (for instance, the name of a person) is input as the subdomain name. In this way, the domain is set by the user who uploads the odor data by entering arbitrary text.

The state information is information indicating the state of the odor sensor 3 that has measured the odor of the object, and includes, for example, the pre-cleaning time, the suction time, the residence time, and the post-cleaning time described above. The pre-cleaning time is time to clean the odor sensor 3 before odor measurement. The suction time is time for the odor sensor 3 to inhale gas (odor). The residence time is time when gas is retained in the gas chamber of the odor sensor 3 for measurement. The post-cleaning time is time to clean the odor sensor 3 after odor measurement. In this way, the state information is used to indicate the acquisition state of the odor data and the maintenance state of the odor sensor 3.

The environmental information is information related to the measurement environment when the odor is measured, and includes, for example, location information and weather information. The location information is geographical information of the measurement location, such as name of area where the odor was measured and GPS (Global Positioning System) coordinate values. The weather information is data indicating the weather condition of the measurement location at the time of odor measurement, for example, "sunny", "rain", or the like.

In addition to location and weather, the environmental information may also include information related to date and time of measurement (for instance, season).

In addition to the odor data, the server 1 inputs the acquisition condition of the odor data, such as the domain name and the state information, to the identification model 141 for learning. By inputting the acquisition condition of the odor data as well, it is possible to make the learning processing closer to human sense. For example, humans are expected to make different judgments (identifications) when smelling a known object (domain) and when smelling an unknown object. Further, they are also expected to make different judgments based on environment (location, weather, or the like) in which they smell the object. Thus, by using the acquisition condition of the odor data as input, it is possible to reproduce the identification result that is closer to human sense.

For instance, the server 1 inputs various information that defines the acquisition condition of the odor data as category variables into the identification model 141. For example, the server 1 provides a layer for category variable input (not shown) in the input layer of the identification model 141 that is different from the layer for odor data input. The server 1 inputs categorical variables indicating such as the domain name, the subdomain name, the state information, or the environmental information to the layer for category variable input and learns them together with the odor data.

The server 1 inputs the odor data for training and the acquisition condition (categorical variable) for training to the identification model 141 and obtains object identification result from the output layer. The server 1 compares the acquired identification result with the correct object (odor name) and optimizes parameters such as weights between the neurons using the error back propagation method so that they approximate each other. In this way, the server 1 obtains the optimal parameters, that is, learned parameters, by identifying objects with identification model 141.

The server 1 stores the learned parameters obtained from the above learning in the learning DB 145 in correspondence with the object (odor name) to be learned and the acquisition condition of the odor data (domain name, or the like). In this way, the server 1 stores the data of the identification model 141 (learned model) generated by machine learning in the learning DB 145.

The server 1 receives upload of the odor data of various objects from the terminal 2 of each user and performs the above machine learning in response to requests from the users. The server 1 stores the learned parameters of the identification model 141 generated in correspondence with the request from each user in the learning DB 145. Thus, the server 1 manages the data of multiple identification models 141 that have learned the odor data of different objects in the learning DB 145.

The server 1 identifies objects based on the identification model 141 in response to request from the terminal 2. Specifically, the server 1 first receives selection input of learned parameter set in the identification model 141 from each learned parameter stored in the learning DB 145 from the terminal 2. The server 1 sets the selected learned parameter to the identification model 141. In this way, the server 1 receives the selection input of the identification model 141 to be used for object identification from the terminal 2.

Next, the server 1 receives selection input from the terminal 2 to select the odor data of the object to be identified among the odor data stored in the odor DB 143. Of course, the server 1 may newly acquire the odor data of the object to be identified from the terminal 2 of the user instead of the odor data already stored in the odor DB 143.

The server 1 reads the selected odor data and the acquisition condition of the odor data from the odor DB 143 and inputs them to the identification model 141 in which the learned parameters are set. Then, the server 1 obtains the identification result of the object corresponding to the input odor data as an output from the identification model 141. Specifically, as described above, the server 1 obtains the probability value of whether or not the object to be identified corresponds to the object learned in the identification model 141. The server 1 outputs the identification result to the terminal 2 for and display the identification result.

From the above, according to the present embodiment, it is possible to identify objects appropriately based on odor by using not only the odor data but also the acquisition conditions of the odor data as input to the identification model 141.

Figure 6:
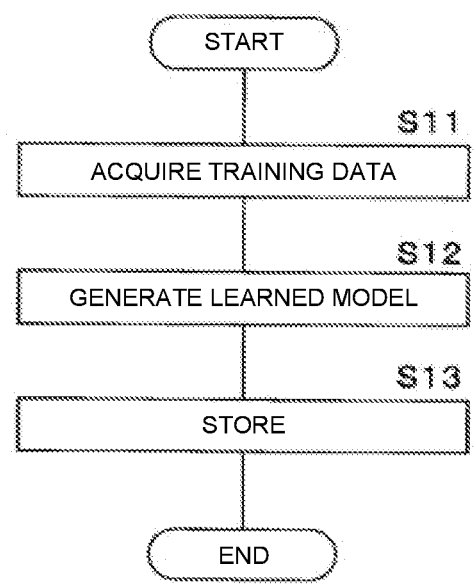
FIG. 6 is a flowchart showing a procedure of generation processing of an identification model.

FIG. 6 is a flowchart showing a procedure of generation processing of the identification model 141. Based on FIG. 6, the processing of generating the identification model 141 by learning the odor data will be described.

The controller 11 of the server 1 acquires training data for generating the identification model 141 from the odor DB 143 (Step S11). The training data is the data in which the correct object (odor name) is associated with the odor data of the object measured by the odor sensor 3 and the acquisition condition of the odor data. The acquisition condition includes the domain name and subdomain name arbitrarily input by the user as text indicating the odor category, the state information indicating the state of the odor sensor 3 such as pre-cleaning time and suction time, and the environmental information such as location information and weather information related to measurement environment of the odor.

Based on the training data, the controller 11 generates the identification model 141 that outputs the identification result of the object using the odor data and the acquisition condition of the odor data as inputs (Step S12). Specifically, as described above, the controller 11 generates a neural network (LSTM) as the identification model 141. The controller 11 inputs the odor data and the category variable indicating the acquisition condition to the identification model 141, and obtains the identification result of that identified the object corresponding to the odor data as an output. The controller 11 compares the acquired identification result with the correct object and generates the identification model 141 by optimizing parameters such as weights between neurons, that is, learned parameters, so that the two are approximated.

The controller 11 stores the learned parameters related to the generated identification model 141 in the learning DB 145 in correspondence with the object (odor name) to be learned and the acquisition condition of the odor data (domain name, etc.) (Step S13) and ends the series of processing.

Figure 7:
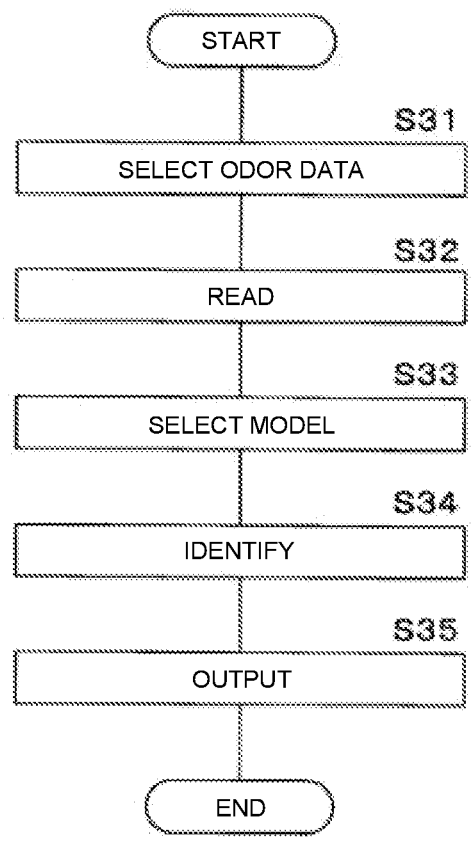
FIG. 7 is a flowchart showing a procedure of an object identification processing.

FIG. 7 is a flowchart showing a procedure of an object identification processing. In FIG. 7, the object identification processing based on the identification model 141 will be described. The controller 11 of the server 1 receives selection input to select the odor data of the object to be identified among the odor data of each object stored in the odor DB 143 (Step S31). The controller 11 reads the selected odor data and the acquisition condition of the odor data from the odor DB 143 (Step S32).

The controller 11 receives the selection input to select the identification model 141 to be used for identifying the object from the terminal 2 (step S33). Specifically, as described above, the controller 11 receives the selection input of the learned parameter to be set in the identification model 141. The controller 11 sets the selected learned parameter to the identification model 141, and inputs odor data and acquisition condition of the object to the identification model 141 to identify the object (Step S34). The controller 11 outputs the identification result to the terminal 2 (Step S35) and ends the series of processing.

From the above, according to the first embodiment, it is possible to identify objects appropriately based on odor.

Further, according to the first embodiment, it is possible to identify objects more appropriately by using the state information indicating the state of the odor sensor 3 as data acquisition condition for input to the identification model 141.

According to the first embodiment, it is possible to identify objects more appropriately based on odor by using the odor sensor 3 with the quartz crystal.

Further, according to the first embodiment, it is possible to identify objects more appropriately by using the environmental information indicating the measurement environment at the time of odor measurement as data acquisition condition for input to the identification model 141.

In addition, according to the first embodiment, it is possible to provide various options (identification model 141) to users by generating a plurality of identification models 141 that perform two-class classification and allowing the users to select the identification model 141 to be used from a plurality of identification models 141.

SECOND EMBODIMENT

In the present embodiment, an embodiment related to UI (User Interface) screen for users to use the identification system described above will be illustrated. Descriptions that overlap with those in the first embodiment are indicated with the same signs and are omitted hereinafter.

FIGS. 8 to 11 show examples of UI screens displayed by the terminal 2. On the UI screen displayed by the terminal 2, menu bars such as "measurement" or "data list" are displayed on the left side of the screen, and the screens in FIGS. 8 to 11 are switched and displayed according to the operation input to each menu. Hereinafter, an overview of the embodiment will be described based on FIGS. 8 to 11.

Figure 8:
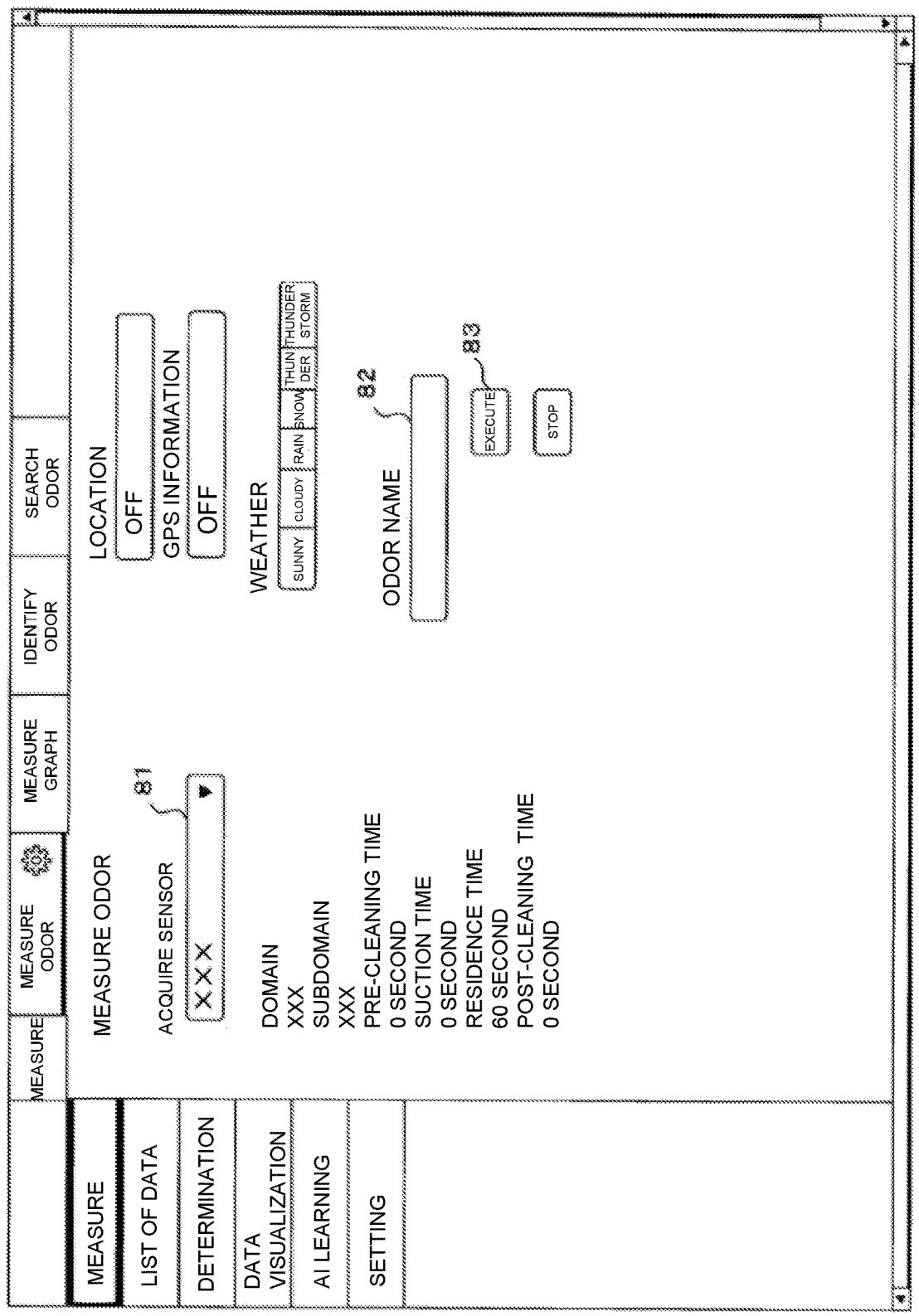
FIG. 8 is an explanatory diagram showing an example of a measurement screen.

FIG. 8 is an explanatory diagram showing an example of a measurement screen. The measurement screen is an operation screen for measuring the odor by the odor sensor 3. The terminal 2 measures the odor in synchronization with the odor sensor 3 connected to the own apparatus corresponding to the operation input on the measurement screen.

Specifically, the terminal 2 receives the selection input of the odor sensor 3 to be used for odor measurement in a sensor selection column 81. When the odor sensor 3 is selected, the acquisition condition of the odor data such as domain name or subdomain name are displayed as default. For example, the server 1 receives registration of the domain name, the subdomain name, and the state information corresponding to the odor sensor 3 used by the user in advance from the user, and stores them in the domain DB 144 in correspondence with the user ID. When the odor sensor 3 of the user is selected in the sensor selection column 81, the domain name or the like registered by the user is set as acquisition condition by default. The setting of the domain name or the like changed by the user may be received on the measurement screen in FIG. 8.

Further, the terminal 2 receives setting input related to the environmental information such as location information and weather information in each column such as "location", "GPS information", and "weather". Finally, the terminal 2 receives the input of the odor name indicating the object to be measured in the odor name input column 82, and starts the odor measurement by the odor sensor 3 corresponding to the operation input to an execution button 83.

The server 1 acquires the measured odor data described above along with the acquisition condition set on the measurement screen, the odor name (correct object), and the like. The server 1 stores each acquired data in the odor DB 143.

FIG. 9 is an explanatory diagram showing an example of a list screen of the odor data. The list screen in FIG. 9 is a display screen showing a list of the odor data stored in the odor DB 143. The user can use the screen to confirm the odor data stored in the odor DB 143.

For example, as shown in FIG. 9, the terminal 2 displays a list of the odor name, the domain name, the subdomain name, the date and time of acquisition of the odor data, and the like in correspondence with each odor data. Furthermore, the user can also search the odor data corresponding to the input to each input column such as "keyword", "domain", "subdomain", and the like displayed at the top of the list screen. Moreover, the user can use the odor data displayed on the list screen for learning and identification.

Figure 10:
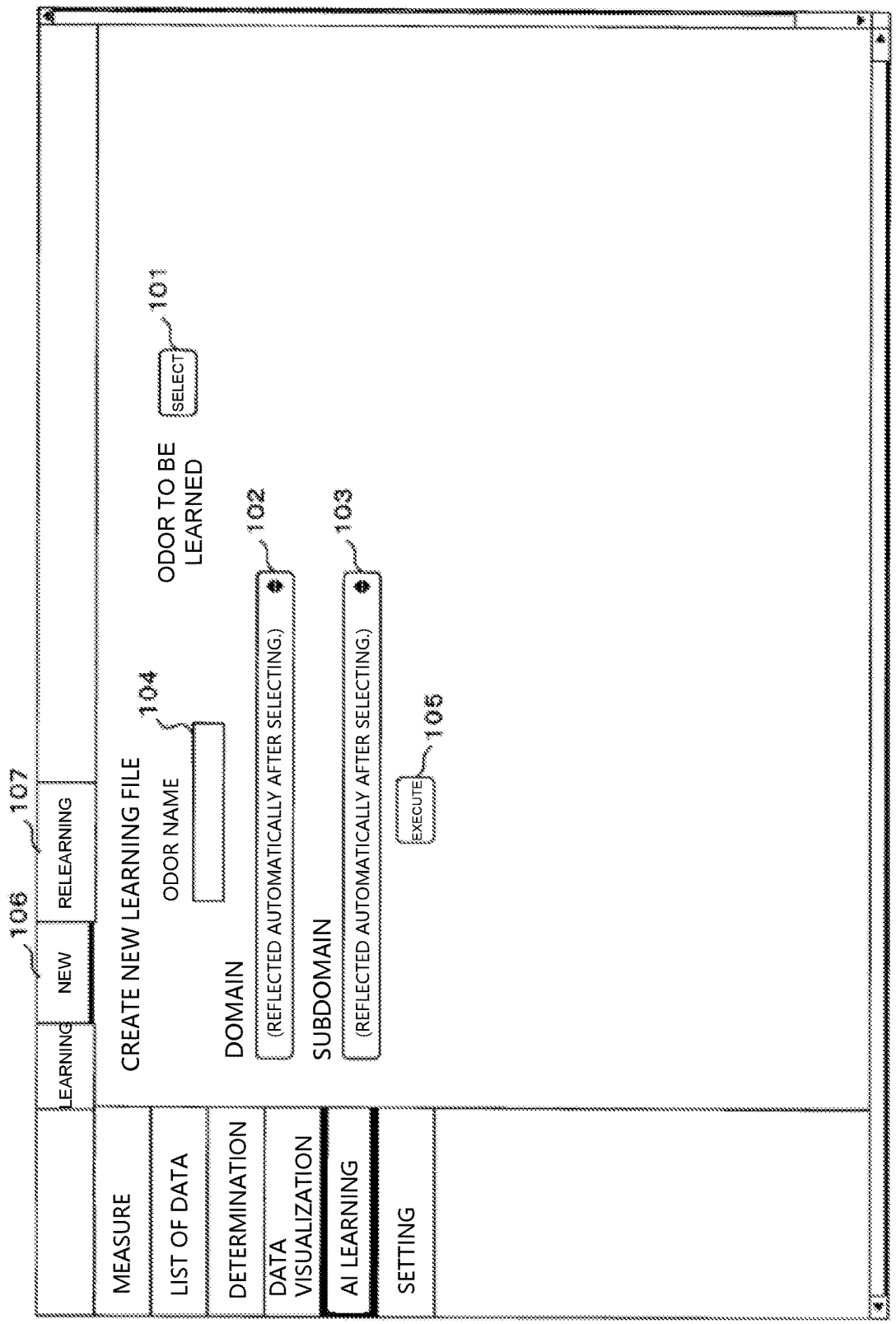
FIG. 10 is an explanatory diagram showing an example of a learning screen.

FIG. 10 is an explanatory diagram showing an example of a learning screen. The learning screen is an operation screen that makes the server 1 to perform learning of the identification model 141. In correspondence with the operation input on the learning screen, the terminal 2 receives the selection input of the odor data to be used as training data and makes the server 1 to execute the generation processing of the identification model 141.

Specifically, based on the operation input to an odor data selection column 101, the terminal 2 receives the selection input to select the odor data to be learned from the odor data stored in the odor DB 143. For example, when the operation input to the odor data selection column 101 is received, the terminal 2 pops up a list of the odor data similar to the list screen in FIG. 9 (not shown). The terminal 2 receives the selection input to select one or more odor data to be learned from the list of the odor data displayed in the pop-up window.

When the odor data to be learned is selected, the domain name and subdomain name corresponding to the selected odor data are displayed as default in a domain selection column 102 and a subdomain selection column 103. The terminal 2 receives setting changes to change the default displayed domain name and subdomain name corresponding to the operation input to the domain selection column 102 and the subdomain selection column 103. In this way, the terminal 2 receives selection input of the acquisition condition (domain name, etc.) of the odor data to be learned along with the odor data.

Moreover, the terminal 2 receives text input of the odor name indicating the object to be learned in an odor name input column 104. In this way, the terminal 2 receives the input of the correct name of the object (correct object) corresponding to the odor data selected in the odor data selection column 101.

In correspondence with the operation input to an execution button 105, the terminal 2 requests the server 1 to perform machine learning based on various information input described above. According to the request from the terminal 2, the server 1 performs machine learning to learn the selected odor data and the acquisition condition and the correct object corresponding to the odor data and generates the identification model 141. The server 1 stores the learned parameters (weights, etc.) of the generated identification model 141 in the learning DB 145 corresponding to the odor name, domain name, and the like.

In the learning screen in FIG. 10, when a new tab 106 at the top of the screen is selected, the server 1 performs learning (generation) of a new identification model 141. On the other hand, when a relearning tab 107 is selected, the server 1 performs relearning to update the identification model 141 that has already been learned. In this case, the terminal 2 receives the selection input to select the learned parameters to be updated, that is, the identification model 141 to be re-learned in addition to the odor data to be learned, the acquisition condition, or the like. The server 1 performs the relearning related to the selected identification model 141 and updates the learned parameters. In this way, the relearning of the identification model 141 can also be performed by the same screen operation in the system.

Figure 11:
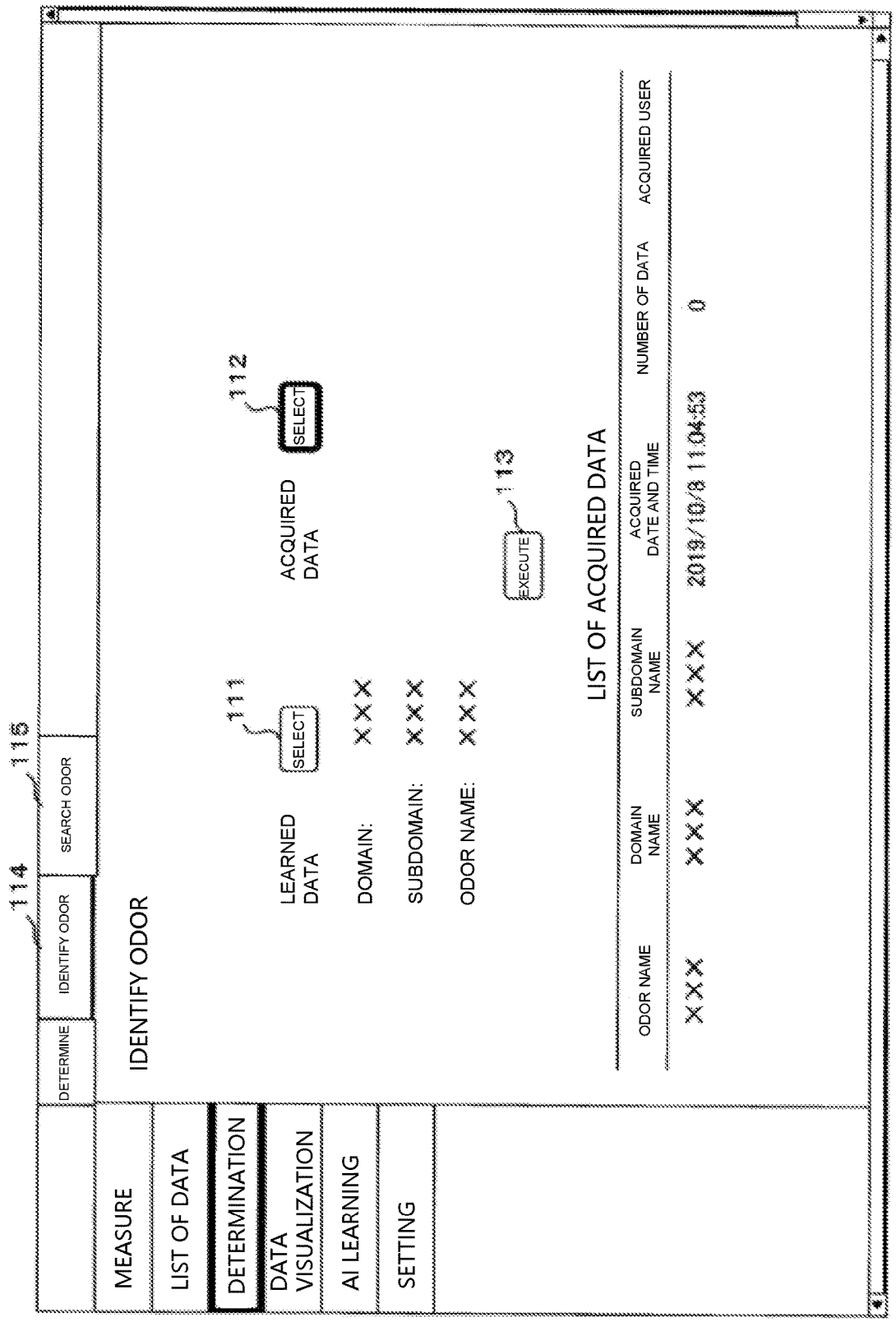
FIG. 11 is an explanatory diagram showing an example of a determination screen.

FIG. 11 is an explanatory diagram showing an example of a determination screen. The determination screen is an operation screen for the server 1 to perform the identification of the object based on the identification model 141 generated above. The terminal 2 makes the server 1 to perform object identification by using the identification model 141 in correspondence with the operation input on the determination screen.

Specifically, the terminal 2 receives the selection input of the learned parameters to be set to the identification model 141 in a learned parameter selection column 111. For example, when the terminal 2 receives the operation input to the learned parameter selection column 111, it displays a pop-up list of information on each learned parameter (data of each identification model 141) stored in the learning DB 145. Specifically, the terminal 2 displays a list of the odor name, the domain name, the subdomain name, or the like stored in the learning DB 145 corresponding to each learned parameter. The terminal 2 receives the selection input to select any of each learned parameter displayed on the list. In this way, the terminal 2 receives the selection input of the identification model 141 used to identify the object.

Next, the terminal 2 receives the selection input of one or more odor data to be identified in an odor data selection column 112. Similar to the learning screen, when receiving the operation input to the odor data selection column 112, the terminal 2 pops up a list of the odor data similar to the list in FIG. 9 and receives the selection input.

When the odor data to be identified is selected, it is preferably that the server 1 determines whether or not the acquisition condition of the odor data (domain name, etc.) is coincident with the acquisition condition of the odor data to be learned in the selected identification model 141 described above, and outputs an error if they do not match. In this way, it is possible to avoid inappropriate situations such as, for instance, using an identification model 141 with a domain name different from the object to be identified.

The terminal 2 receives the operation input to an execution button 113 and requests the server 1 to identify the object. In correspondence with the request from the terminal 2, the server 1 sets the learned parameters selected in the learned parameter selection column 111 to the identification model 141, and inputs the odor data selected in the odor data selection column 112 to the identification model 141 to identify the object. Specifically, the server 1 identifies each of the one or more odor data selected in the odor data selection column 112, and outputs the identification result (probability value) of each odor data to the terminal 2. The terminal 2 displays the identification result of each odor data output from the server 1.

On the determination screen, an identification tab 114 and a search tab 115 are displayed at the top of the screen. When the identification tab 114 is selected, the terminal 2 makes the server 1 to perform the identification of the object according to the procedure described above. On the other hand, when the search tab 115 is selected, the terminal 2 makes the server 1 to perform the identification (search) of the object using one or more identification models 141.

Specifically, the terminal 2 receives the selection input to select one or more learned parameters corresponding to a selection input to the learned parameter selection column 111 on the determination screen similar to that of FIG. 11. In this way, the terminal 2 receives the selection input to select one or more identification models 141 to be used for object identification. When a plurality of identification models 141 are selected, the server 1 inputs the odor data selected in the odor data selection column 112 to each of the selected identification models 141, and obtains the identification results from each of the identification models 141. In this way, the server 1 identifies whether or not the object to be identified corresponds to each object to be learned by each identification model 141, and identifies multiple objects simultaneously.

Based on the identification results in each identification model 141, the server 1 outputs an identification result (search result) to identify which of the objects corresponding to each identification model 141 corresponds to the object according to the input odor data. For instance, the server 1 ranks the objects according to the probability values output from each identification model 141, and outputs the object names in descending order of the probability values. Alternatively, the server 1 may output the object name with the highest probability value as the search result.

As described in the first embodiment, it is possible to prepare an identification model 141 capable of multi-class classification by having one identification model 141 learn the odor data of multiple objects, but the identification accuracy can be improved by making the identification model 141 as a model that performs two-class classification.

By combining a plurality of these identification models 141, it is possible to determine the correspondence between a specific odor and a plurality objects, that is, multi-class classification can be performed suitably.

Figure 12:
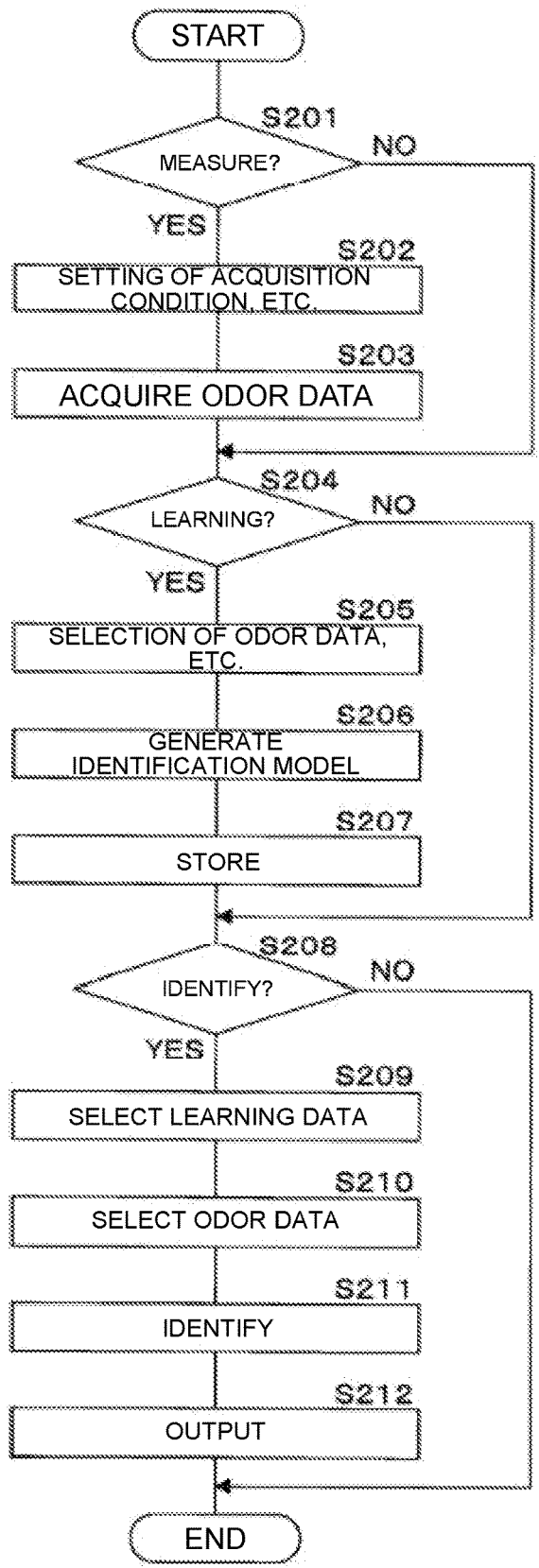
FIG. 12 is a flowchart showing an example of a processing procedure executed by the server according to the second embodiment.

FIG. 12 is a flowchart showing an example of a processing procedure executed by the server 1 according to the second embodiment.

The controller 11 of the server 1 determines whether or not to measure the odor data in response to the operation input in the terminal 2 (step S201). If it is determined that measurement of the odor data is to be performed (S201: YES), the controller 11 receives the odor name indicating the object to be measured (correct object) as well as the setting input of the acquisition condition of the odor data from the terminal 2 (Step S202). The terminal 2 performs measurement by the odor sensor 3 in response to the operation input from the user, and the controller 11 of the server 1 acquires odor data from the odor sensor 3 via the terminal 2 and stores the odor data in the odor DB 143 in correspondence with the acquisition condition or the like set in step S202 (step S203).

After executing the processing of step S203, or in the case of NO in step S201, the controller 11 determines whether or not to perform the learning of the odor data in response to the operation input in the terminal 2 (step S204). If it is determined that learning is to be performed (S204: YES), the controller 11 receives a selection input from the terminal 2 to select the odor data to be learned (Step S205). Specifically, as described above, the controller 11 receives setting input of the odor data to be learned as well as the acquisition condition of the odor data, the correct object, or the like.

The controller 11 performs machine learning based on the selected odor data, the acquisition conditions of the odor data, and the input correct object, and generates the identification model 141 (Step S206). The controller 11 stores the learned parameters of the generated identification model 141 in the learning DB 145 (Step S207).

After performing the processing of step S207, or in the case of NO in step S204, the controller 11 determines whether or not to identify the odor data in response to the operation input in the terminal 2 (step S208). If it is determined that the identification of the odor data is to be performed (S208: YES), the controller 11 receives the selection input to select the identification model 141 to be used for identification of the odor data (step S209). Specifically, as described above, the controller 11 receives the selection input to select the learned parameter set in the identification model 141.

The controller 11 receives the selection input to select the odor data to be identified (Step S210). The controller 11 sets the learned parameter selected in step S209 to the identification model 141 and inputs the odor data selected in step S210 to identify the object (step S211). The controller 11 outputs the identification result to the terminal 2 (Step S212). After performing the processing of step S212, or in the case of NO in step S208, the controller 11 ends the series of processing.

Overall, according to the second embodiment, it is possible to provide users with a platform that can learn and identify odor data with simple operations.

The embodiments described in the present invention are presented as examples and are not intended to limit the scope of the invention. The scope of the present invention is not in the sense described above but is indicated by the claims, and it is intended to include all modifications within the scope of the claims and the equivalent scope thereof.

The invention claimed is:

1. An information processing apparatus, comprising:
a controller configured to execute a program so as to:
acquire target odor data measuring an odor of a target object via an odor sensor using a quartz crystal, the target odor data corresponding to time-series data of frequencies, the frequencies being measured while the odor of the target object is in an inner space of the odor sensor for a predetermined period of time;
acquire a target acquisition condition of the target odor data, the target acquisition condition including environmental information regarding a measurement environment in which the odor of the target object is measured, the environmental information including location information or weather information of the measurement environment;
store data of a plurality of learned models obtained by learning sample odor data and a sample acquisition condition including the location information or the weather information with respect to a plurality of different sample objects, and each of the plurality of learned models having:
an input layer accepting the sample odor data as the time-series data of the frequencies together with the sample acquisition condition in association with the plurality of different sample objects;
an intermediate layer extracting of a plurality of sample features of the sample odor data from the input layer in association with the plurality of different sample objects; and
an output layer providing an identification result based on the plurality of different sample features;
receive an operation input from a user via an operation interface to select a target model of the plurality of learned models;
input the target odor data as the time-series data of the frequencies together with the target acquisition condition into the input layer of the target model;
cause the intermediate layer of the target model to extract a target feature of the target odor data;
cause the output layer of the target model to provide a target identification result based on the target feature and the plurality of sample features of the target model;
identify the target object based on the target identification result; and
display information relating to the identified target object,
wherein the target identification result corresponds to a probability value indicating how likely the target object corresponds to one of the plurality of different sample objects.

2. The information processing apparatus in claim 1, wherein:
each of the target and sample acquisition conditions includes text data indicating a category of the odor, and the text data is input via the operation interface by a measurement user who measures the odor.

3. The information processing apparatus in claim 1, wherein:
each of the target and sample acquisition conditions includes state information indicating a state of the odor sensor when measuring the odor.

4. The information processing apparatus in claim 1, wherein:
the target identification result includes information indicating whether the target object corresponding to the target odor data corresponds to one of the plurality of different sample objects.

5. The information processing apparatus in claim 1, wherein:
the information processing apparatus is configured to be connected to a terminal of the user, and
the operation input is received from the terminal.

6. An information processing method for causing a processor to execute a program, the information processing method comprising executing on the processor the steps of:
acquiring target odor data measuring an odor of a target object via an odor sensor using a quartz crystal, the target odor data corresponding to time-series data of frequencies, the frequencies being measured while the odor of the target object is in an inner space of the odor sensor for a predetermined period of time;
acquiring a target acquisition condition of the target odor data, the target acquisition condition including environmental information regarding a measurement environment in which the odor of the target object is measured, the environmental information including location information or weather information of the measurement environment;
storing data of a plurality of learned models obtained by learning sample odor data and a sample acquisition condition including the location information or the weather information with respect to a plurality of different sample objects, and each of the plurality of learned models having:
an input layer accepting the sample odor data as the time-series data of the frequencies together with the sample acquisition condition in association with the plurality of different sample objects;
an intermediate layer extracting of a plurality of sample features of the sample odor data from the input layer in association with the plurality of different sample objects; and
an output layer providing an identification result based on the plurality of different sample features;
receiving an operation input from a user via an operation interface to select a target model of the plurality of learned models;
inputting the target odor data as the time-series data of the frequencies together with the target acquisition condition into the input layer of the target model;
causing the intermediate layer of the target model to extract a target feature of the target odor data;
causing the output layer of the target model to provide a target identification result based on the target feature and the plurality of sample features of the target model;
identifying the target object based on the target identification result; and
displaying information relating to the identified target object,
wherein the target identification result corresponds to a probability value indicating how likely the target object corresponds to one of the plurality of different sample objects.

7. The information processing method in claim 6, wherein:
each of the target and sample acquisition conditions includes text data indicating a category of the odor, and the text data is input via the operation interface by a measurement user who measures the odor.

8. The information processing method in claim 6, wherein:
each of the target and sample acquisition conditions includes state information indicating a state of the odor sensor when measuring the odor.

9. The information processing method in claim 6, wherein:
the target identification result includes information indicating whether the target object corresponding to the target odor data corresponds to one of the plurality of different sample objects.

10. A non-transitory computer-readable medium storing a program for causing a computer to execute a process by a processor so as to perform the steps of:
acquiring target odor data measuring an odor of a target object via an odor sensor using a quartz crystal, the target odor data corresponding to time-series data of frequencies, the frequencies being measured while the odor of the target object is in an inner space of the odor sensor for a predetermined period of time;
acquiring a target acquisition condition of the target odor data, the target acquisition condition including environmental information regarding a measurement environment in which the odor of the target object is measured, the environmental information including location information or weather information of the measurement environment;
storing data of a plurality of learned models obtained by learning sample odor data and a sample acquisition condition including the location information or the weather information with respect to a plurality of different sample objects, and each of the plurality of learned models having:
an input layer accepting the sample odor data as the time-series data of the frequencies together with the sample acquisition condition in association with the plurality of different sample objects;
an intermediate layer extracting of a plurality of sample features of the sample odor data from the input layer in association with the plurality of different sample objects; and
an output layer providing an identification result based on the plurality of different sample features;
receiving an operation input from a user via an operation interface to select a target model of the plurality of learned models;
inputting the target odor data as the time-series data of the frequencies together with the target acquisition condition into the input layer of the target model;
causing the intermediate layer of the target model to extract a target feature of the target odor data;
causing the output layer of the target model to provide a target identification result based on the target feature and the plurality of sample features of the target model;
identifying the target object based on the target identification result; and
displaying information relating to the identified target object,
wherein the target identification result corresponds to a probability value indicating how likely the target object corresponds to one of the plurality of different sample objects.

11. The non-transitory computer-readable medium according to claim 10, wherein:
   each of the target and sample acquisition conditions includes text data indicating a category of the odor, and the text data is input via the operation interface by a measurement user who measures the odor.

12. The non-transitory computer-readable medium according to claim 10, wherein:
   each of the target and sample acquisition conditions includes state information indicating a state of the odor sensor when measuring the odor.

13. The non-transitory computer-readable medium according to claim 10, wherein:
   the target identification result includes information indicating whether the target object corresponding to the target odor data corresponds to one of the plurality of different sample objects.

* * * * *